United States Patent [19]

Lee

[11] 4,208,483

[45] Jun. 17, 1980

[54] TISSUE CULTURE SYSTEM

[75] Inventor: Harold H. Lee, Toledo, Ohio

[73] Assignee: The University of Toledo, Toledo, Ohio

[21] Appl. No.: 944,267

[22] Filed: Sep. 21, 1978

[51] Int. Cl.² .............................................. C12M 3/00
[52] U.S. Cl. ..................................... 435/284; 435/313
[58] Field of Search ....................... 195/127, 139, 142; 435/284, 313

[56] References Cited

U.S. PATENT DOCUMENTS

| | | | |
|---|---|---|---|
| 3,028,314 | 4/1962 | Means et al. ...................... | 195/127 X |
| 3,062,724 | 11/1962 | Reusser ............................ | 195/127 X |
| 3,839,155 | 10/1974 | McAleer et al. ................... | 195/127 |
| 4,004,981 | 1/1977 | Hurni et al. ...................... | 195/127 |
| 4,065,359 | 12/1977 | Hurni ................................ | 195/127 |

Primary Examiner—R. B. Penland
Attorney, Agent, or Firm—Wilson, Fraser, Barker & Clemens

[57] ABSTRACT

A tissue culture system for zero gravity high-density cultivation of eucaryotic cells requiring attachment to a substratum in order to differentiate is disclosed. A major component of the system is a cylindrical bottle filled with culture medium and having mounted therein a rotatable shaft. The shaft includes a plurality of collagen-treated discs projecting therefrom and at an angle to the shaft to provide the necessary attachment substratum and to impel the culture medium as the shaft is rotated. Means are provided for initial stocking of the bottle with the culture cells and for continuously supplying fresh medium to and removing waste medium from the bottle.

4 Claims, 2 Drawing Figures

TISSUE CULTURE SYSTEM

BACKGROUND OF THE INVENTION

This invention relates to a high-density tissue culture system utilizing zero gravity to facilitate the cultivation of eucaryotic cells that require attachment to substratum to differentiate and to produce desired products of biomedical interests.

Many biological products such as hormone releasing factors from hypothalamus are difficult to isolate in large quantities by conventional biochemical extraction procedures since their presence is in minute quantities. With current advancement of recombinant DNA studies, it is possible to produce large quantities of "pure" products if their molecular sizes are not larger than insulin molecules. For larger molecules, isolations and insertions of the genes are exceedingly difficult because there may be more cistrons required than just the structural genes themselves. Thus, utilization of eucaryotic cell lines or primary cultures that synthesize specialized products is more practical.

For most normal differentiated cells, a substratum and attachment are required for them to proliferate, to differentiate, and to synthesize specialized products. A large surface area is required to obtain large cell members.

One system which has been particularly successful in large scale culture of cells requiring substratum attachment utilizes roller bottles. The interior of the roller bottle provides the necessary growing surface, and rotation of the bottle provides a continuous exchange of nutrient and gas between the medium therein and the eucaryotic cells. However, to obtain cell culture on a large scale, a lot of bottles are needed which requires a large room for the roller racks.

Suspension culture has been relatively successful in application to cells which do not require stratum attachment to proliferate and differentiate. However, as the cell density increases, the cells adhere to each other and settle to the bottom of the culture vessel. There, either the cells undergo contact inhibition of growth, the gaseous exchange between the underlayers of cells and the medium is impaired, or the toxic metabolic waste accumulates and harms the cells. Further, a spinner is necessary to suspend and maintain suspension of the cells but the spinner generates shearing forces which are injurious to the suspended cells.

SUMMARY OF THE INVENTION

The present invention is a high-density tissue culture system which is compact and yet provides a greater area for cellular attachment than prior art systems.

The system includes a cylindrical bottle filled with culture medium and having mounted therein a rotatable shaft. The shaft has a plurality of collagen-treated discs circumferentially projecting therefrom and at an angle to the shaft to provide the required attachment substratum and to impel the culture medium as the shaft is rotated. Cellular attachment can occur on either side of the discs and only minimal gas is essential between the discs, such that a vast surface area for attachment is available in a small space.

The system is initiated in space or other zero or low gravity environments so that sedimentation of the cell or cell line stock does not occur. Also, the zero gravity environment facilitates uniform dispersion of air throughout the culture medium.

Now speed rotation of the disc shaft is capable of gently encouraging the cells toward the discs to promote attachment thereto without injuring the cells, and uniform attachment on both sides of the discs is accomplished by periodically reversing the direction of rotation during the attachment period. After attachment, means are available for continuously supply fresh culture medium to the vessel and removing waste therefrom. Also, after attachment, the system may be returned to a gravity environment and growth sustained to synthesize desired cellular products.

It is therefore an object of the present invention to provide a high density tissue culture system.

It is also an object to provide a tissue culture system for use in low gravity environments.

Other objects and advantages will be obvious to persons skilled in the art in view of the following detailed description of a preferred embodiment.

DETAILED DESCRIPTION OF THE INVENTION

Figure 1:
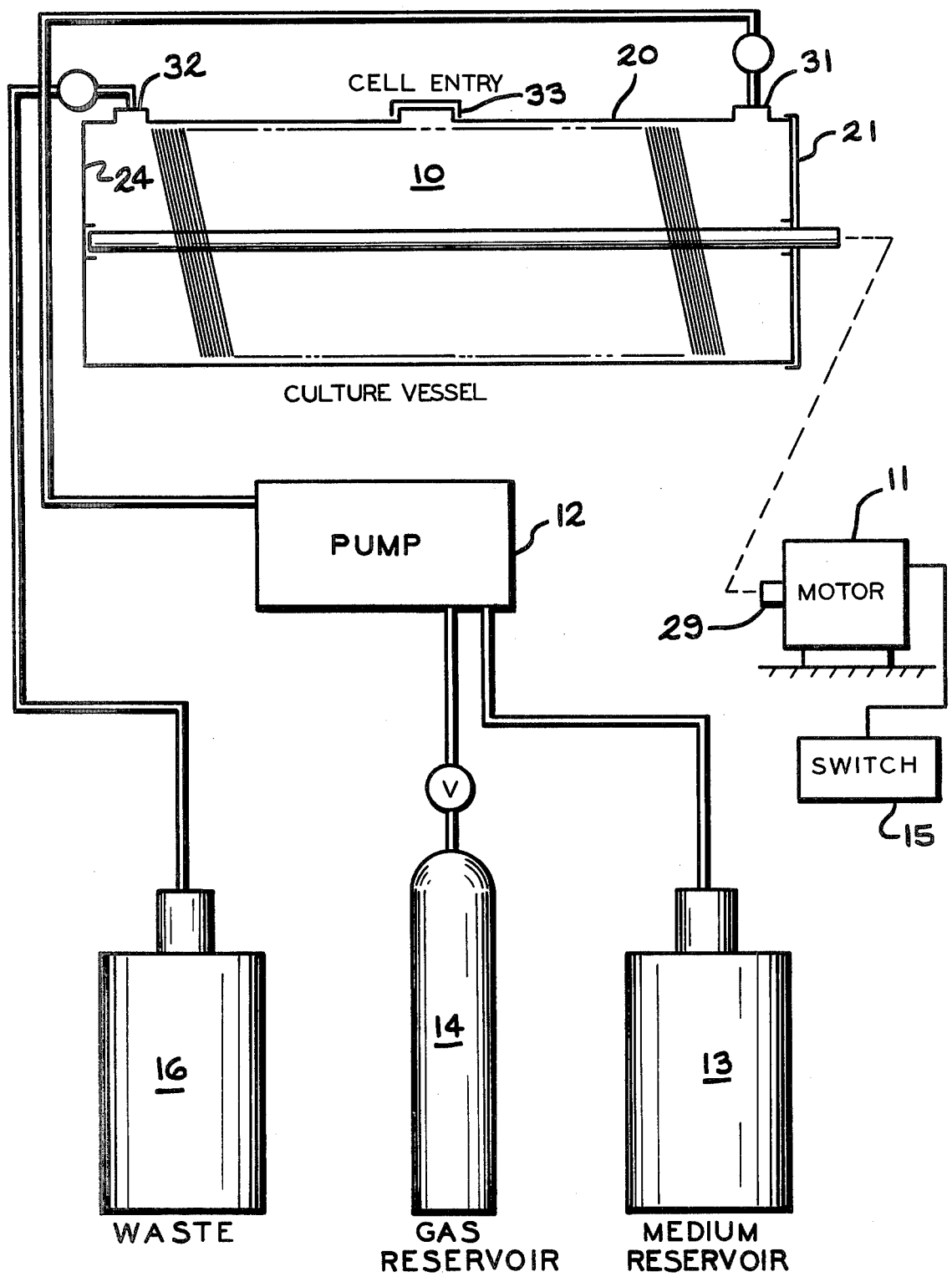
FIG. 1 is an overall schematic view of a preferred embodiment of a tissue culture system in accordance with the present invention.

FIG. 1 illustrates a preferred embodiment of the total culture system in accordance with the present invention. The system generally comprises a culture vessel 10, a reversible electric motor 11, a pulsating pump 12, a liquid medium reservoir 13, a gas reservoir 14, an automatic timer switch 15 to reverse the direction of rotation of the electric motor 11, and a waste reservoir 16.

Figure 2:
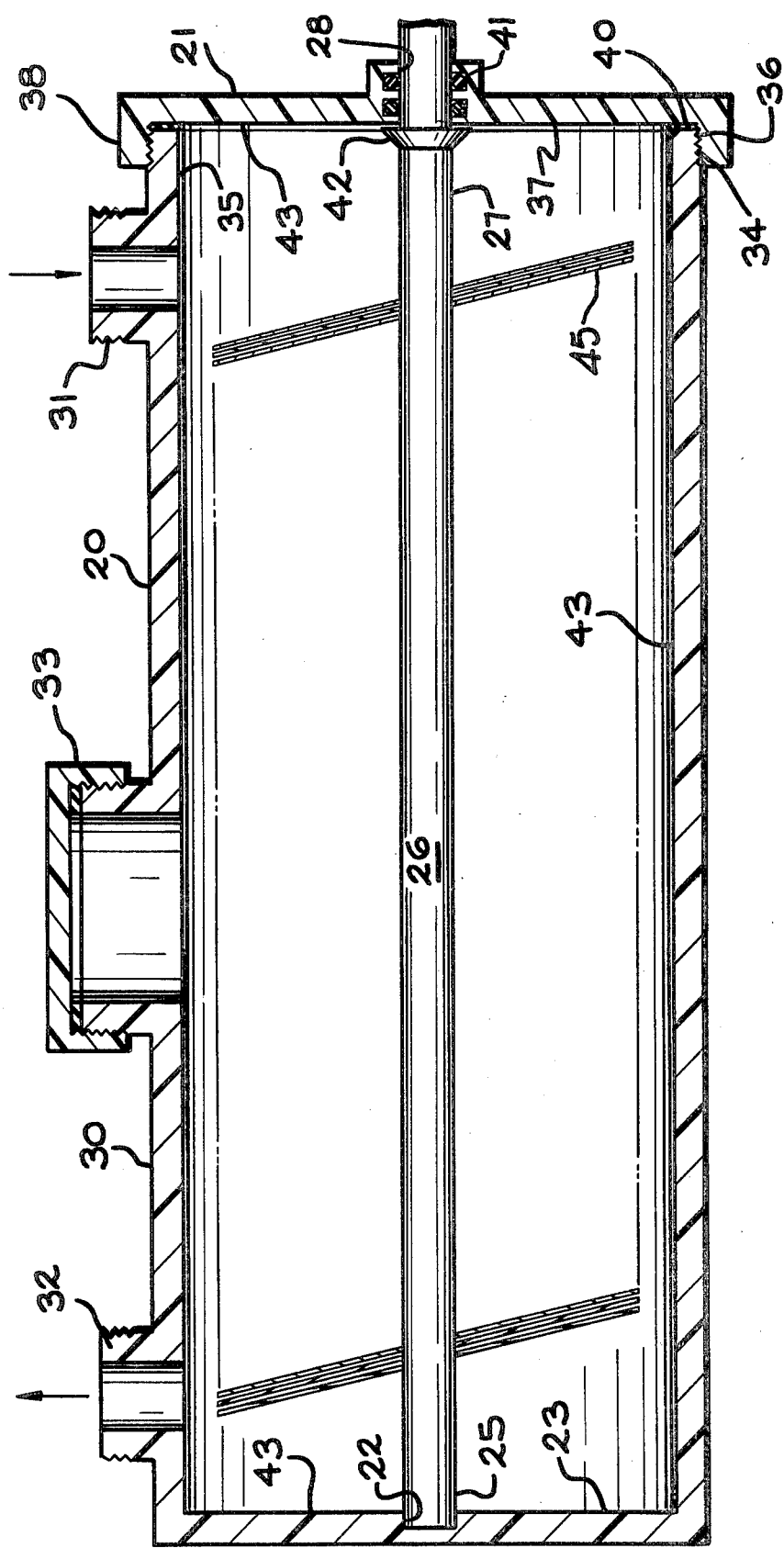
FIG. 2 is a detailed view of the culture vessel shown in FIG. 1.

The culture vessel 10, shown in greater detail in FIG. 2, consists of a cylindrical open-topped body 20 and a cap 21. The body 20 includes a recess 22 in the interior 23 of its base 24 in which is mounted one end 25 of a shaft 26, the other end 27 of the shaft 26 extending through an opening 28 in the cap 21 and attaching to the driven portion 29 of the motor 11. The cylindrical exterior 30 of the body 20 has an inlet 31 and an outlet 32 at opposite ends thereof for delivery and discharge of fresh and waste medium respectively, and a centrally positioned entry 33 for stocking cells and cell lines. The exterior 30 of the body 20 also includes threads 34 adjacent its open end 35 for engagement with complementary threads 36 around the interior 37 of a downwardly extending cylindrical lip 38 on the cap 21.

A ring seal 40, preferably made of soft silicone rubber, extends about the interior periphery of the cap 21 to render a water tight seal between the cap 21 and the body 20 of the vessel 10. O-rings 41 seated within the opening 28 of the cap 21 seal against leakage therethrough, and a collar 42 secures the shaft 26 from movement in the axial direction. The interior 43 of the vessel 10 is silicone treated so that the culture cells do not attach thereto. Preferably, but not necessarily, the vessel 10 and the cap 21 themselves are constructed of plexiglass.

Attachment or culture discs 45 are integrally secured to the shaft 26 at such an angle that their slow rotation generates enough motion to cause gentle collision between the cells or cell lines and the surfaces of the discs 45. A preferred angle for such purposes is 60° relative to the axis of the shaft 26. The discs 45 are coated with collagen to promote cell attachment. Also, the discs 45 may include perforations or other passages therethrough to aid in medium circulation and waste removal. Still further, other appendages may be substituted for the discs, such as a series of fan blades or a continuous helix, without departing from the intended scope of the invention.

Examples or primary cells which may be cultured in the above-described apparatus include mouse embryo cultures, chick embryo cultures, junvenile cockeral Leydig cells, and mouse liver cells. Useful cell lines, obtained from the American Type Culture Collection, include BHK-21 (baby hamster kidney), CCL-21C Chang liver cell (human), Hak (Syriah hamster kidney), and PK15 (porcine kidney). The above cells are useful because of their differentiated products or their virus producing capabilities.

The culture system of the present invention is designed for use in space or other low or zero gravity environments and preferably at room temperature. Preliminary to the addition of the cell stocks to the vessel 10, the vessel 10 is filled with an appropriate liquid growth medium, cell lines are diluted to appropriate concentrations, and primary cells are prepared in Ca-deficient, EDTA-containing or trypsin-containing medium, or other suitable material to prevent aggregation prior to feeding the culture vessel 10.

Cell stocks are added to the vessel 10 in a low or zero gravity environment by a syringe via the centrally positioned entry 33. Since their is no sedimentation of the cells at zero gravity, attachment is solely dependent upon random collision of cells with the discs 45. To facilitate cellular attachment to the collagen-coated discs 45, in addition to the Brownian movement and motility of the cells themselves, the motor 11, and consequently the angularly oriented discs, are rotated at a slow rate to gently agitate the medium. Even distribution of the cells upon both sides of the discs 45 is accomplished by periodic reversals of the direction of rotation such that the cells are pushed backward and forward. Reversal of the direction of rotation of the discs 45 also prevents accumulations of cells at one end or a particular area of the vessel 10. In the above-described embodiment, since the interior 43 of the vessel 10 is silicone treated, the cells will not attach themselves thereto. However, it should be apparent that other arrangements are possible. It should also be apparent that only minimal clearance between the discs 45 is necessary and, therefore, a large number of discs 45 may be accommodated on the shaft 26, thereby allowing a great number of cells to be grown in each vessel 10.

After cell attachment to the discs 45, gas, preferably air with 5% $CO_2$, is pumped into the vessel 10 to displace a quantity of the medium, and then both the medium and the gas are fed through the vessel 10 at a sufficient rate to maintain cell growth therein. Because of zero or low gravity, the gas is randomly and uniformly intermixed with the medium to facilitate gaseous exchange with the cells. The discs 45 may be rotated at a faster rate after cellular attachment to further assist in medium replenishment and gaseous exchange. The feed rates, rotation speed and gas and liquid medium compositions are dependent upon cell type.

Once cellular attachment and growth is completed, the entire system may be removed to gravity environment and life maintained within the vessel 10 to continuously synthesize and purify the desired cellular product associated with the particular cell type, or for further scientific investigation, depending upon the intended purpose of the particular system.

Although the above description provides considerable detail relating to a preferred embodiment of the present invention, modifications thereto will be obvious to persons skilled in the art without departing from the intended scope of the invention as set forth in the following claims.

What I claim is:

1. A tissue culture system for use in zero or low gravity for cultivating cells that require attachment to a substratum to differentiate, said system comprising a culture vessel substantially filled with culture medium, a shaft rotatably mounted within said vessel, a plurality of discs that provide a substratum for attachment of the cells thereon, said discs being secured to said shaft and projecting circumferentially therefrom at an angle of about 60 degrees to the shaft, means for rotating said shaft in either direction whereby said discs impel said medium, and means for cell entry and for supplying fresh medium and removing waste medium.

2. A tissue culture system, as defined in claim 1, wherein said means for cell entry and for supplying fresh medium and removing waste medium include gas and liquid medium reservoirs, a waste reservoir, a valved opening in said culture vessel for supply of said gas and liquid medium thereto, a valved opening in said culture vessel for waste removal, a feed entry for supplying said vessel with such cells to be cultivated, and a pump for continuously supplying gas and liquid medium from said reservoirs to said gas and liquid medium valved opening and for removing waste through said waste removal opening to said waste reservoir.

3. A tissue culture system, as defined in claim 1, wherein said shaft rotating means is a reversible motor.

4. A tissue culture system for cultivating cells that require attachment to a substratum to differentiate for use in low or zero gravity, said system comprising:
 a culture vessel substantially filled with culture medium, said vessel including a cylindrical body having a closed bottom and an open-mouth, a cap positioned over and sealingly engaging said open mouth and having a central hole therethrough, valved openings for culture medium supply into said vessel and waste removal therefrom, a feed entry for supply of the cells to be cultivated, and means for rotatably mounting a shaft;
 a shaft extending through said cap central hole and mounted on said shaft mounting means within said vessel, said shaft including a plurality of discs secured thereto and projecting circumferentially therefrom within said vessel and at an angle of about 60 degrees to said shaft whereby rotation of said shaft results in said disks impelling said culture medium, said disks providing a substratum for attachment of the cells;
 a means for selectively rotating said shaft in either direction; and
 a means for continuously supplying culture medium to said culture medium opening and into said vessel and for removing waste from said vessel through said waste removal opening.

* * * * *